US009089445B2

(12) United States Patent
Agnew et al.

(10) Patent No.: US 9,089,445 B2
(45) Date of Patent: Jul. 28, 2015

(54) STENT WITH PROTECTED BARBS

(75) Inventors: Carl Agnew, West Lafayette, IN (US);
Jason Bowe, West Lafayette, IN (US);
Kurt Dierking, Louisville, KY (US);
Jarin Kratzberg, Lafayette, IL (US);
Alan Leewood, Lafayette, IN (US);
David Orr, Piedmont, SC (US)

(73) Assignee: Cook Medical Technologies LLC,
Bloomington, IN (US)

( * ) Notice: Subject to any disclaimer, the term of this patent is extended or adjusted under 35 U.S.C. 154(b) by 207 days.

(21) Appl. No.: 13/266,228

(22) PCT Filed: Apr. 27, 2010

(86) PCT No.: PCT/US2010/032569
§ 371 (c)(1),
(2), (4) Date: Jan. 9, 2012

(87) PCT Pub. No.: WO2010/126889
PCT Pub. Date: Nov. 4, 2010

(65) Prior Publication Data
US 2012/0130470 A1    May 24, 2012

Related U.S. Application Data

(60) Provisional application No. 61/172,987, filed on Apr. 27, 2009.

(51) Int. Cl.
*A61F 2/06* (2013.01)
*A61F 2/86* (2013.01)
(Continued)

(52) U.S. Cl.
CPC ... *A61F 2/86* (2013.01); *A61F 2/95* (2013.01); *A61F 2002/8483* (2013.01); *A61F 2210/0004* (2013.01); *A61F 2220/0016* (2013.01); *A61F 2250/0071* (2013.01)

(58) Field of Classification Search
CPC ............ A61F 2/848; A61F 2/86; A61F 2/95; A61F 2002/8483; A61F 2002/8486; A61F 2220/0016; A61F 2250/0071
USPC ........................ 600/200; 623/1.11, 1.12, 1.36
See application file for complete search history.

(56) References Cited

U.S. PATENT DOCUMENTS

| 5,167,614 A | 12/1992 | Tessmann et al. |
| 5,383,926 A * | 1/1995 | Lock et al. ..................... 623/1.2 |

(Continued)

FOREIGN PATENT DOCUMENTS

| WO | WO 01/10342 A1 | 2/2001 |
| WO | WO 01/76509 A1 | 10/2001 |

(Continued)

OTHER PUBLICATIONS

International Search Report for International Application No. PCT/US2010/032569, dated Jul. 23, 2010 (3 pages).

*Primary Examiner* — Alexander Orkin
(74) *Attorney, Agent, or Firm* — Brinks Gilson & Lione (57) ABSTRACT

An endoluminal prosthesis is described and comprises a stent (40), At least one barb (42) secured to the stent, and a degradable barb guard (52) covering at least a portion of the barb and protecting the distal tip when the stent is in a compressed configuration. The barb guard (52) comprises a degradable structure that degrades to expose the distal tip of the barb when the stent is placed in a vessel. An endoluminal prosthesis deployment system comprising a sheath having a lumen and a prosthesis within the sheath lumen is also described.

20 Claims, 4 Drawing Sheets

(51) Int. Cl.
*A61F 2/95* (2013.01)
*A61F 2/848* (2013.01)

(56) References Cited

U.S. PATENT DOCUMENTS

| | | | |
|---|---|---|---|
| 5,591,197 A * | 1/1997 | Orth et al. | 623/1.16 |
| 6,146,416 A * | 11/2000 | Andersen et al. | 623/1.15 |
| 6,214,025 B1 | 4/2001 | Thistle et al. | |
| 6,517,573 B1 * | 2/2003 | Pollock et al. | 623/1.15 |
| 6,878,161 B2 * | 4/2005 | Lenker | 623/1.13 |
| 2003/0208227 A1 | 11/2003 | Thomas | |
| 2005/0159803 A1 | 7/2005 | Lad et al. | |
| 2005/0240259 A1 * | 10/2005 | Sisken et al. | 623/1.36 |
| 2006/0122684 A1 * | 6/2006 | Lye et al. | 623/1.2 |
| 2007/0100432 A1 * | 5/2007 | Case et al. | 623/1.15 |
| 2008/0033534 A1 | 2/2008 | Cook et al. | |
| 2009/0005803 A1 * | 1/2009 | Batiste | 606/200 |
| 2009/0048664 A1 | 2/2009 | Cage | |
| 2009/0306703 A1 * | 12/2009 | Kashkarov et al. | 606/200 |
| 2010/0161033 A1 * | 6/2010 | Jantzen et al. | 623/1.16 |

FOREIGN PATENT DOCUMENTS

| | | |
|---|---|---|
| WO | WO 2005/077303 A2 | 8/2005 |
| WO | WO 2007/079413 A2 | 7/2007 |

* cited by examiner

STENT WITH PROTECTED BARBS

REFERENCE TO EARLIER FILED APPLICATIONS

This application is a 371 national phase of PCT/US2010/032569, filed Apr. 27, 2010, and claims the benefit under 35 U.S.C. §119(e) of U.S. Provisional Application No. 61/172,987, filed Apr. 27, 2009, the disclosures of which are incorporated, in their entirety, by this reference.

TECHNICAL FIELD

This invention relates to medical devices and, in particular, to devices, systems, and methods for anchoring a prosthesis such as an implantable medical device in a body lumen.

BACKGROUND ART

Deploying an endoluminal prosthesis into the vessel of a patient from a remote location is generally known. An endoluminal prosthesis, such as a stent or stent graft, is introduced into a vessel in a radially constrained state. Once the prosthesis is positioned, it can then be expanded within the vessel. The prosthesis may employ one or more barbs that can engage the vessel wall to limit movement of the prosthesis within the vessel.

An endoluminal prosthesis is typically introduced into a vessel via a delivery and deployment device. Such a device may include a cover or sheath that is placed within the vessel. The prosthesis is manipulated within the sheath into the vessel. The sheath is retracted from the prosthesis to allow the prosthesis to expand within the vessel. If the prosthesis is self-expanding, it will expand within the vessel when it is no longer constrained by the sheath. If the prosthesis is balloon expanded, a balloon will be required to expand the device after the sheath is removed. U.S. Pub. Pat. App. Nos. 2004/0098079, 2004/0106974, 2005/0085890, and 2005/0060018, which are herein incorporated by reference, disclose various examples of prostheses and devices for delivering and deploying a prosthesis.

When a prosthesis is disposed within a sheath, at least a portion of the prosthesis engages the sheath in frictional contact. Such frictional engagement may be sufficiently high so as to create significant interference between the stent and the sheath. This is particularly the case when the prosthesis is self-expanding or when the prosthesis has one or more exposed barbs that engage the inner surface of the sheath. Such frictional engagement may result in increased operating effort to remove the sheath from the device.

DISCLOSURE OF THE INVENTION

The present invention seeks to provide an improved implantable medical device provided with barbs, an improved barb arrangement for implantable medical devices and an improved method and system for deploying implantable medical devices.

According to an aspect of the present invention, there is provided an endoluminal prosthesis as specified in claim 1.

According to another aspect of the present invention, there is provided an endoluminal prosthesis deployment system as specified in claim 8.

Various devices, systems, and methods are disclosed throughout the specification and in the drawings. In one example, an endoluminal prosthesis is described and comprises a stent having a compressed configuration and an expanded configuration, a barb secured to the stent and having a distal tip, and a degradable barb guard covering at least a portion of the barb and protecting the distal tip when the stent is in the compressed configuration. The barb guard comprises a degradable structure that degrades to expose the distal tip of the barb when the stent is placed in a vessel. The exposed distal tip will thus be able to engage a surrounding vessel where the unexposed tip would not.

The guard may comprise any degradable structure, for example, a dissolvable structure or a frangible structure. Thus, in some examples, the barb guard degrades by dissolving to expose the distal tip of the barb when the stent is placed in a vessel and, in some examples, the barb guard degrades by breaking to expose the distal tip of the barb when the stent is placed in a vessel. The barb guard may be attached directly to the stent and, in some cases, directly to the barb.

In another example, an endoluminal prosthesis system comprises a sheath having a sheath lumen and a prosthesis disposed within the sheath lumen. The prosthesis comprises a stent and a barb secured to the stent. The barb comprises a distal tip and a degradable barb guard covering at least a portion of the barb and preventing direct contact between the distal tip of the barb and the sheath. The barb guard comprises a degradable structure, such as a dissolvable or frangible structure, that degrades to expose the distal tip of the barb after the stent is released from the sheath.

In some examples, the barb guard may contact the sheath when the stent is disposed within the sheath. The barb may be biased towards an extended configuration and have a bias force that is greater than the strength of the guard. In these examples, the guard will break when the stent is released from the sheath. The guard may comprise any degradable structure, such as a dissolvable and/or frangible structure.

The term prosthesis as used herein is intended to be understood in a broad manner and to include any implantable medical device such as stents, stent grafts, vena cava filters, occluders, prosthetic valves and so on.

According to another aspect of the present invention, there is provided a method of deploying an implantable medical device provided with one or more barbs, including the steps of covering or otherwise protecting said barb or barbs by a removable covering provided on the medical device, said covering being degradable or frangible upon deployment of the device.

BRIEF DESCRIPTION OF THE DRAWINGS

Embodiments of the present invention are described below, by way of example only, with reference to the accompanying drawings, in which.

TERMINOLOGY

Throughout the specification, when referring to a barb or a portion thereof, the terms "distal" and "distally" shall denote a position, direction, or orientation along the barb that is generally towards, or in the direction of, the anchor. The terms "proximal" and "proximally" shall denote a position, direction, or orientation along the barb that is generally away from, or in the opposite direction of, the anchor.

The term "prosthesis" means any device, object, or structure that supports, repairs, or replaces, or is configured to support, repair, or replace a body part or a function of that body part. It can also mean a device that enhances or adds functionality to a physiological system. Examples of prostheses include stents, stent grafts, vessel occlusion devices, vena cava filters, and the like.

The term "stent" means any device or structure that provides, or is configured to provide, rigidity, expansion force, or support to a body part (e.g., a diseased, damaged, or otherwise compromised body lumen.). A stent may comprise any suitable material, including, but not limited to, biocompatible metals and plastics. Examples of suitable materials include metals such as stainless steel and NITINOL, and plastics such as polyethylene terephthalate ("PET"), polytetrafluoroethylene ("PTFE") and polyurethane.

A stent may be "expandable," that is, it may be capable of being expanded from a constricted configuration to an expanded configuration. A stent may be self-expanding and expand by virtue of its own resilience. Alternatively, a stent may be pressure-expandable and expand only upon the application of an external force. In addition, a stent may be expandable upon application of heat, such as when exposed to body temperature. An example of a self-expanding stent is the Z-STENT®, which is available from Cook Incorporated, Bloomington, Ind., USA.

A stent may comprise one or more barbs. A barb may comprise a suitable biocompatible material, such as a biocompatible metal or plastic. Suitable biocompatible materials include the stent materials described above. Where the stent comprises a metal, the barb and the stent may comprise the same or a similar material. For example, the materials may have similar electromotive forces. Such a construction may minimize corrosion at the junction between the barb and the stent.

The term "secured" refers to a structure that is "connected," "joined," "attached," and the like. "Secured" is not limited to a particular method or manner of connecting, joining, or attaching. Thus, a barb "secured" to a stent refers to barb-stent structures formed by connecting, joining, or attaching independently formed structures (such as by welding, soldering, or the like), as well as monolithic barb-stent structures.

The term "degradable" refers to a structure that is capable of degrading within a medically effective timeframe. "Degrading" includes tearing, breaking, severing, fracturing, dissolving, dissociating, and the like. Terms such as "tearable," "breakable," "severable," "fracturable," "dissolvable," "dissociable," and the like, may be used and refer to structures that are capable of degrading, as described, within a medically effective timeframe.

A structure is not "degradable" merely because it is capable of degrading over an indeterminate period of time. As defined, the structure must be capable of degrading over a medically effective timeframe. A medically effective timeframe depends on many factors, including the type of device and procedure. In some examples, the timeframe may be less than a second. In other examples, the timeframe may be minutes or more. A structure that is capable of degrading in a period of an hour is not "degradable," as that term is used herein, if the medical procedure warrants that the structure degrade in less than a second. On the other hand, such a structure may be "degradable," as that term is used herein, if the medical procedure allows for the structure to degrade within, for example, 24 hours.

The term "frangible" means readily or easily torn, broken, severed, fractured, or the like.

The term "lumen" describes a cavity or channel within a tube or a tubular body, such as body vessel. The term "endoluminal" means within a lumen, and can refer to objects that are found or that can be placed within a lumen, or methods or processes that occur within a lumen. An "endoluminal prosthesis" is thus a prosthesis that is found, or that can be placed, within a lumen. Examples of endoluminal prostheses include, but are not limited to, stents, grafts, stent grafts, venous or aortal valves, and vena cava filters. An endoluminal prosthesis may be generally tubular and comprise one or more lumens. Examples of tubular prostheses include straight, branched, and bifurcated prostheses.

The term "score" refers to a channel, depression, cut, score, notch, line, perforation, aperture, or the like, and includes both recessed structures as well as projected structures. The term "score" may also refer to a series of channels, depressions, cuts, scores, notches, lines, perforations, apertures, or the like. A score may be provided by any mechanical, thermal, or chemical means known in the art, such as cutting by knife or carbide tip, by sanding, by chemical etching, by laser scoring, or by molding.

The term "monolithic" refers to structures that are formed as a single piece, rather than being separately formed and attached.

DESCRIPTION OF THE PREFERRED EMBODIMENTS

Figure 1:
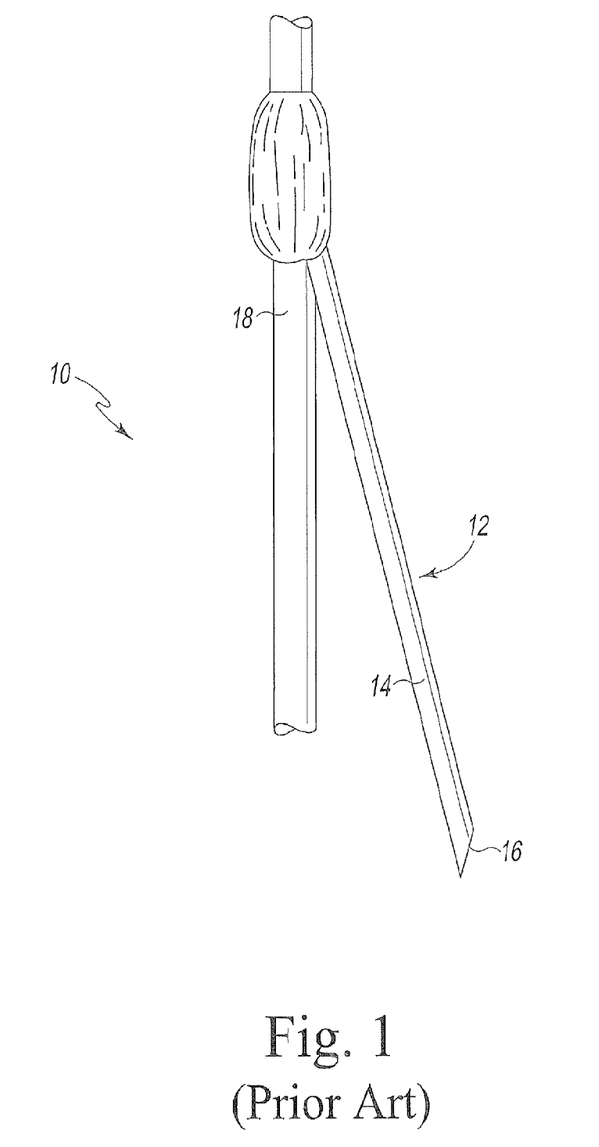
FIG. 1 depicts a portion of a stent and a barb.

FIG. 1 depicts a prior art stent 10 with a barb 12. The barb 12 has a barb body 14 that extends distally towards a barb tip 16. The tip 16 is preferably sharp and, when the stent is inserted into a vessel, can engage the vessel to limit movement of the stent within the vessel. In this example, the barb 12 is fixedly attached to a strut 18 of the stent 10 via weld, solder, adhesive or the like. In other examples, the barb 12 and the stent 10 may be monolithic. In other examples, the barb 12 may be variably, rather than fixedly, attached to the stent. Examples of barbs and attachment techniques are disclosed, for example, in U.S. Pub. Pat. App. Nos. 2003/0236570 A1 and 2005/0240259 A1. Each of these references is herein incorporated by reference.

The barb of FIG. 1 is shown in an extended configuration. The distal tip 16 extends outwardly from the stent 10 in this configuration. The distal tip 16 is unprotected and may engage tissue of a vessel in which the stent 10 is placed. The barb 12 may have a retracted configuration (not shown) whereby the distal tip 16 is retracted towards the stent 10, away from the extended configuration. This may be advantageous, for example, when the stent is compressed within a sheath. In typical devices, the distal tip 16 is unprotected in the retracted configuration and, therefore, is still able to engage the sheath during delivery and deployment. This engagement may be minimal if the barb is oriented in the direction of sheath withdrawal. If, however, the barb is oriented against the direction of sheath withdrawal, then the unprotected tip 16 may dig into the sheath, increasing the deployment effort.

Figure 2A:
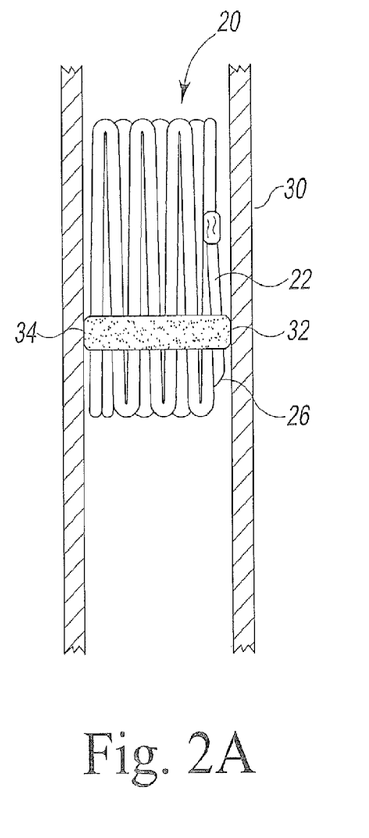
FIG. 2A depicts an example of a stent and a degradable barb guard, with the stent disposed in a contracted state within the lumen of a sheath.

FIG. 2A depicts an example of a stent 20 in a constricted configuration, disposed within the lumen of a sheath 30. The stent 20 has a barb 22, shown in a retracted configuration. The stent may comprise additional barbs as necessary or desired. A barb guard 32 covers a portion of the barb 22 and protects the distal tip 26. As shown, the barb guard 32 is disposed between the barb 22 and the sheath 30 and prevents direct contact between the tip 26 and the sheath. Thus, the barb guard 32 prevents the tip 26 from engaging the sheath during delivery.

Figure 2B:
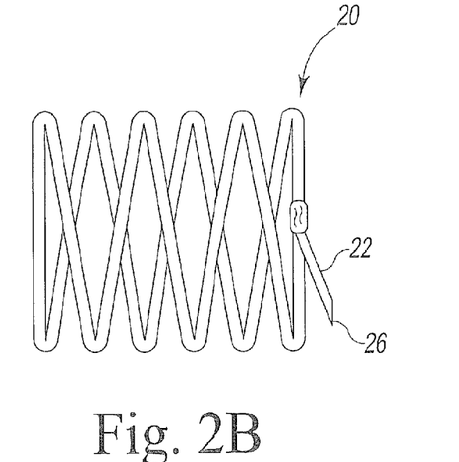
FIG. 2B depicts the stent of FIG. 2A in an expanded state.

FIG. 2B depicts stent 20 after it has been released from the sheath 30. The stent 20 expands to an expanded configuration and the barb 22 extends to an extended configuration. The barb guard 32 no longer covers barb 22 and the distal tip 26 is unprotected. Accordingly, the distal tip 26 is free to engage a surrounding vessel.

The barb guard 32 has a degradable structure that degrades to release the barb 22 from the barb guard 32. For example, the barb guard 32 may comprise a material that readily dissolves or dissociates after the stent 20 is released into a vessel. In these examples, the barb 22 is released, and the distal tip 26 exposed, by virtue of the dissolution or dissociation of the barb guard 32.

Examples of suitable dissolvable materials include, but are not limited to, synthetic materials such as polylactides, polyglycolides, and polyvinyl acetate, or natural materials such as gelatin. The material is preferably formulated to dissolve over a narrow temperature range at or below body temperature, for example between 25-35° C., or 30-35° C. The material is preferably stable at temperatures below this range. In particular, the material is preferably stable in the presence of fluids, such as saline or heparin, that are exposed to the stent during pre-procedural preparation.

In the example shown in FIG. 2A, the barb guard 32 comprises a dissolvable strip or band 34 that is disposed about the periphery of the stent 20. The band 34 may be disposed about the entire periphery of the stent and retain the entire stent in a constricted configuration. Alternatively, a band may be provided that is disposed about only a portion of the stent. For example, the band may be disposed about fewer than all of the stent struts. If the stent 20 is self-expanding, it will exert an expansion force against the barb guard 32. In some examples, the barb guard 32 may have a tensile strength that is greater than the force exerted by the stent 20, and the stent will not be able to expand. In these examples, the band 34 preferably comprises a material that dissolves relatively quickly (e.g., in a matter of seconds), so that the tensile strength of the band 34 becomes less than the force exerted by the stent 20. At that point, the band 34 will break under the pressure exerted by the stent and allow the barb 22 to extend and the distal tip 26 to engage the vessel.

In other examples, the dissolvable band 34 may have an initial tensile strength that is less than the force exerted by the stent 20. In these examples, the band 34 can break with little or no dissolution. Accordingly, the band may comprise a material that dissolves more slowly, for example, in a matter of minutes or hours.

Figure 3:
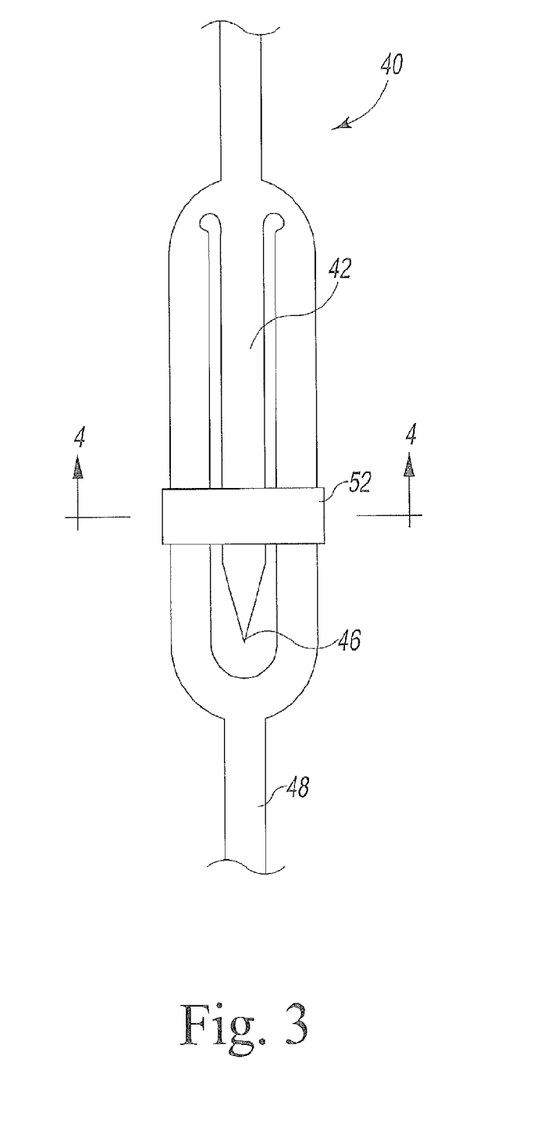
FIG. 3 depicts another example of a degradable barb guard.

FIG. 3 depicts a stent 40 with a degradable barb guard 52 disposed about a single strut 48 and barb 42. In this example, the barb 42 is monolithic with the stent 40 and may be formed, for example, by cutting from a cannula. The barb 42 is preferably biased towards an extended configuration where the distal tip 46 extends away from the strut 48. In this example, the barb guard 52 holds the barb 42 in a retracted configuration and protects the distal tip 46. The guard 52 prevents the barb 42 from springing towards the extended configuration and prevents direct contact between the tip 46 and a sheath (not shown) when the stent 40 is placed in the sheath.

The barb guard 52 may comprise a material that is dissolvable, as described above with reference to FIG. 2A. Additionally, or alternatively, the barb guard may comprise a frangible material. In a preferred example, the biasing force of the barb 42 is greater than the initial strength of the barb guard 52. When the stent 40 is compressed in a sheath (not shown), the sheath provides a counterbalance to the biasing force of the barb, preventing the barb from extending. When the stent 40 is released from the sheath, however, the barb 42 presses against the barb guard 52 with a force that is sufficient to degrade the guard. The guard breaks, tears, severs, or the like, allowing the distal tip 46 to extend outwardly and to engage a surrounding vessel.

The barb guard 52 may comprise any suitable biocompatible material. Examples of suitable materials include synthetic materials, such as polylactides, polyglycolides, polyvinyl acetate, polyester, polytetrafluoroethylene (PTFE), and polyurethane, and natural materials such as gelatin, extracellular matrix (ECM), and small intestinal submucosa (SIS). The guard 52 may be attached to the barb 42 and/or the stent 40 by any suitable process. For example, the guard may be formed as an independent strip or band and folded, wrapped, stretched, or otherwise placed about the barb and strut. A suitable biocompatible adhesive may be used to fix the guard to the stent, if necessary. In some examples, the guard may be molded or cast with the stent and barb. In other examples, the guard may be formed independently of the stent (e.g., by molding, extruding, casting, or the like) and attached to the stent in a separate step.

Figure 4:
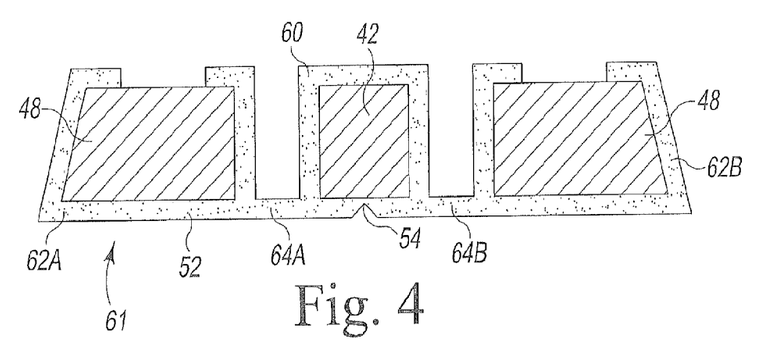
FIG. 4 depicts an example of a barb guard, and the stent of FIG. 3, in cross-section.

FIG. 4 depicts a cross-sectional view of the stent 40 shown in FIG. 3 and an exemplary degradable barb guard 52. In this example, the barb guard retains the barb 42 and comprises a frangible structure that breaks to release the barb and expose the distal tip 46. The guard 52 has a three-point attachment system 61 that attaches to the stent 40 and retains the barb 42 in a retracted configuration. The attachment system 61 here includes a retaining structure 60 and strut attachments 62A, 62B. The barb 42 is positioned within the retaining structure 60, which, in the example shown, engages and retains the barb about its entire periphery. Attachments 62A, 62B are configured to form a "snap-on" attachment with strut 48. The barb 42 may be placed within the retaining structure 60 by sliding the structure onto the barb, for example, when the barb is in its extended configuration. The barb can then be retracted to its retracted configuration and the attachments 62A, 62B snapped into place at respective portions of the strut 48. Bridge structures 64A, 64B connect the retaining structure 60 and attachments 62A, 62B and form a relatively linear connection therebetween.

The stent 40 may then be placed within a sheath with the barb guard 52 retaining the barb 42 in a retracted configuration. The barb 42 is biased towards the extended configuration and, therefore, exerts a biasing force when it is in the retracted configuration. The sheath counterbalances the biasing force of the barb, preventing the barb from acting on the barb guard 52. The barb guard 52 protects the distal tip 46 and prevents direct contact between the distal tip and the sheath. When the stent 40 is released from the sheath, the barb 42, no longer constrained by the sheath, will exert its biasing force against the guard 52. The frangible retaining structure 60 will break to release the barb 42 and expose the distal tip 46.

As shown in FIG. 4, the barb guard 52 may comprise a score 54. The score 54 acts as a stress-riser and facilitates degradation of the guard. The biasing force of the barb 42 is preferably greater than the strength of the barb guard 52 so that the guard breaks at the score 54 when the stent is released from the sheath. When the guard 52 breaks, the barb 42 becomes unprotected and the distal tip 46 can extend outwardly. At this point, the barb guard is still secured to the stent via attachments 62A, 62B and bridge structures 64A, 64B. The barb guard may remain attached to the structure throughout the life of the prosthesis. Alternatively, the barb guard may comprise a dissolvable material, as described above, that dissolves over a period of time, for example over days, weeks, or months.

Figure 5:
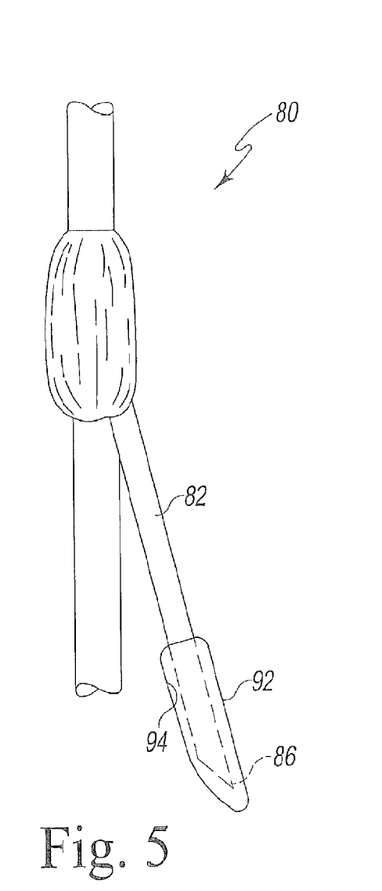
FIG. 5 depicts another example of a degradable barb guard.

FIG. 5 depicts another example of a stent 80 with a degradable barb guard 92. In this example, the guard comprises a degradable blunt cap 94, hereinafter referred to as a blunt, that covers the distal tip 86 of the barb 82. The blunt 94 may be provided, for example, by applying a degradable material over the distal tip 86. Suitable applications include dipping, molding, and the like. The degradable blunt 94 covers and protects the distal tip 86 and, when the stent is disposed within a sheath, prevents direct contact between the distal tip and the sheath. The blunt 94 is preferably made of a material that dissolves or dissociates as the stent is released into a vessel, as described above with reference to FIG. 2A. The material is preferably formulated so that the blunt dissolves quickly (e.g., in seconds), to allow the distal tip 86 to engage the vessel immediately after the stent 80 is expanded.

Throughout this specification various indications have been given as to preferred and alternative embodiments of the invention. However, it should be understood that the invention is not limited to any one of these. It is therefore intended that the foregoing detailed description be regarded as illustrative rather than limiting.

The disclosures in U.S. patent application No. 61/172,987, from which this patent application claims priority, and in the abstract accompanying this application, are incorporated herein by reference.

The invention claimed is:

1. An endoluminal prosthesis comprising:
   a stent configurable between a compressed configuration within a sheath and an expanded configuration and having at least one strut;
   at least one barb secured to the at least one strut and comprising a distal tip, the at least one barb having a retracted configuration toward the strut and an extended configuration biased away from the strut, wherein the at least one barb is moveable between the retracted configuration and the extended configuration; and
   at least one degradable barb guard disposed about the at least one strut and the at least one barb and covering at least a portion of the barb and holding it in the retracted configuration and protecting the distal tip when the stent is in the compressed configuration;
   wherein the barb guard comprises a degradable structure that degrades to expose the distal tip of the barb when the stent is placed in a vessel.

2. The prosthesis of claim 1, where the guard comprises a dissolvable structure.

3. The prosthesis of claim 2, where the guard covers the distal tip of the barb.

4. The prosthesis of claim 1, where the guard comprises a frangible structure.

5. The prosthesis of claim 4, where the frangible structure comprises a score and is configured to break at the score.

6. The prosthesis of claim 4, wherein the guard comprises a dissolvable structure.

7. The prosthesis of claim 1, wherein the guard is attached directly to the barb.

8. An endoluminal prosthesis deployment system comprising:
   a sheath having a sheath lumen; and
   a prosthesis disposed within the sheath lumen and comprising a stent having at least one strut and at least one barb secured to the at least one strut, the at least one barb and the at least one strut having a circumference, wherein the at least one barb comprises a distal tip; and
   at least one degradable barb guard disposed substantially about the circumference of the at least one strut and the at least one barb and covering at least a portion of the barb and preventing direct contact between the distal tip of the and the sheath;
   wherein the guard comprises a degradable structure that degrades to expose the distal tip of the barb after the stent is released from the sheath; and
   wherein the at least one barb is movable between a retracted configuration and an extended configuration.

9. The deployment system of claim 8, wherein the guard contacts the sheath.

10. The deployment system of claim 8 wherein when the barb is in the extended configuration it has a bias force that is greater than the strength of the guard so that the guard breaks when the stent is released from the sheath.

11. The deployment system of claim 10, wherein the guard comprises a frangible structure.

12. The deployment system of claim 8, wherein the guard comprises a dissolvable structure.

13. The deployment system of claim 8, wherein the guard comprises a blunt cover that covers the distal tip of the barb.

14. The deployment system of claim 13, wherein the guard comprises a frangible structure.

15. The deployment system of claim 14, wherein the frangible structure comprises a score and is configured to break at the score.

16. The deployment system of claim 8, wherein the guard is attached directly to the barb.

17. A method of deploying in a lumen an endoluminal prosthesis covered by a sheath, the endoluminal prosthesis having a plurality of struts and at least one barb attached to a strut of the plurality of struts, the barb having a first configuration toward the strut and a second configuration biased away from the strut, and
   a degradable structure disposed about the strut and the at least one barb and holding the barb in the first configuration and preventing direct contact between each barb and the sheath, the method comprising:
   retracting the sheath to expose the endoluminal prosthesis;
   expanding said endoluminal prosthesis to an expanded state;
   degrading the degradable structure and
   moving the barb from the first configuration to the second configuration thereby engaging each barb with the lumen.

18. The method of claim 17 wherein the endoluminal prosthesis is self expanding.

19. The method of claim 17 wherein the endoluminal prosthesis is balloon expandable.

20. The method of claim 17 wherein the degradable structure is frangible and wherein the degradable structure is degraded by breaking the degradable structure.

* * * * *

UNITED STATES PATENT AND TRADEMARK OFFICE
CERTIFICATE OF CORRECTION

PATENT NO.         : 9,089,445 B2
APPLICATION NO.    : 13/266228
DATED              : July 28, 2015
INVENTOR(S)        : Carl Agnew et al.

Page 1 of 1

It is certified that error appears in the above-identified patent and that said Letters Patent is hereby corrected as shown below:

On the Title Page

Right column, item (57), line 9, under "ABSTRACT", before "within the sheath" replace "prostesis" with --prosthesis--.

Signed and Sealed this
Twelfth Day of January, 2016

Michelle K. Lee
*Director of the United States Patent and Trademark Office*